United States Patent
Romaschin et al.

(12)

(10) Patent No.: US 6,306,614 B1
(45) Date of Patent: *Oct. 23, 2001

(54) MEASUREMENT OF ANALYTES IN WHOLE BLOOD

(75) Inventors: Alexander D. Romaschin, Etobicoke; Paul M. Walker, Toronto, both of (CA)

(73) Assignee: Sepsis, Inc., Toronto (CA)

( * ) Notice: Subject to any disclaimer, the term of this patent is extended or adjusted under 35 U.S.C. 154(b) by 0 days.

This patent is subject to a terminal disclaimer.

(21) Appl. No.: 09/353,189

(22) Filed: Jul. 14, 1999

Related U.S. Application Data

(63) Continuation-in-part of application No. 08/552,145, filed on Nov. 2, 1995, now Pat. No. 5,804,370, which is a continuation-in-part of application No. 08/516,204, filed on Aug. 17, 1995, now abandoned, which is a continuation of application No. 08/257,627, filed on Jun. 8, 1994, now abandoned.

(51) Int. Cl.[7] .................. G01N 33/53; G01N 33/354; C12Q 1/70; C12Q 1/37
(52) U.S. Cl. ................ 435/7.2; 435/5; 435/7.1; 435/7.24; 435/7.31; 435/7.32; 435/24; 435/34; 435/962; 435/968; 435/975; 436/513; 436/518; 436/536; 436/808; 436/811
(58) Field of Search ................... 435/5, 7.1, 7.2, 435/7.24, 7.31–7.37, 25, 34, 38, 962, 968, 973, 975; 436/513, 518, 536, 539, 808–811

(56) References Cited

U.S. PATENT DOCUMENTS

| | | | |
|---|---|---|---|
| 4,737,455 | * | 4/1988 | De Baetselier ........................ 435/7 |
| 5,804,370 | * | 9/1998 | Romaschin et al. .................... 435/5 |
| 6,203,997 | * | 3/2001 | Romanchin et al. ................. 435/7.2 |

FOREIGN PATENT DOCUMENTS

94/29728 * 12/1994 (WO).

OTHER PUBLICATIONS

Lillus et al; J.Bioluminescence and Chemiluminescence, 7(2) 117–122, 1992.*

Romaschin et al Clinical Chemistry; 42 (6), Abstract No. A146, 1996.*

* cited by examiner

*Primary Examiner*—Lynette R. F. Smith
*Assistant Examiner*—Padma Baskar
(74) *Attorney, Agent, or Firm*—Klauber & Jackson

(57) ABSTRACT

The invention relates to a method for measuring the level of a preselected analyte in a sample of blood of a human or animal patient by incubating the test sample with an antibody specific to the analyte to form an immunocomplex, which then interacts with the white blood cell fractions and result in the production of oxidants. Oxidants are detected using chemiluminescent reagents. The assay is performed on the sample and in addition includes a measurement of the oxidant production resulting from a maximal stimulatory dose of immunocomplexes, providing a ratio to indicate the level of analyte in the sample. The white blood cell oxidant response may be enhanced by the inclusion of certain agents such as zymosan. This method may be used to determine levels of analytes in a sample of a patient's blood including endotoxin and other analytes related to sepsis, in order to select the proper therapeutic course, or may be used to measure other analytes such as inflammatory mediators, hormones, acute phase proteins, toxins, drugs of abuse, markers of cardiac muscle damage, therapeutic drugs, cytokines, and chemokines. Additional parameters derived from the assay include maximal chemiluminscent response and responsiveness to aid in the staging of sepsis.

15 Claims, 1 Drawing Sheet

MEASUREMENT OF ANALYTES IN WHOLE BLOOD

CROSS-REFERENCE TO RELATED APPLICATIONS

This application is a continuation-in-part of application Ser. No. 08/552,145, filed Nov. 2, 1995, now U.S. Pat. No. 5,804,370, which is a continuation-in-part of application Ser. No. 08/516,204, filed Aug. 17, 1995, abandoned, which is a continuation of application Ser. No. 08/257,627, filed Jun. 8, 1994, abandoned.

FIELD OF THE INVENTION

This invention relates generally to methods to measurement of the level of an analyte in a sample of blood. Analytes may include infectious miicroorganisms, their toxic products, inflammatory mcdiators, hormones, acute phase proteins, toxins, drugs of abuse, nlarkecrs of cardiac muscle damagye, therapeutic drugs, cytokines, chemokines, and others.

DEFINITIONS

"Analyte" is defined as the specific substance of interest present in a bodily fluid sample and being analyzed by tlhe methods of thei present invention. In the case of analytes related to infection and sepsis, these may include, for example, microorganisms and their components, including gram positive cell wall constituents and gram negative endotoxin, lipopolysaccharide. lipoteichoic acid, and the inflammatory mediators that appear in circulation as a result of the presence of these components, including tumor necrosis factor (TNF), interleukin-1 (IL-1) and other interleukins and cytokines. Other analytes may include drugs of abuse, hormones, toxins. therapeutic drugs, markers of cardiac muscle damage, etc.

"Sepsis" is defined as a pathological condition of the body resulting from the presence of infectious microorganisms, which clinically manifests as one or more of the following sequelae: pyrexia, hypotension, hypoxcmia, tachycardia, hypothermia, neutroplhilia, and neutropenia.

"Immunocomplexes" is a synonym for antibody-antigen complexes.

"Opsonized" refers to a particle to which immunoglobulin and complement factors are bound and which results in a more vigorous recognition of the particle by the immune system. For example. the yeast polysaccharide zymosan, or latex particles, may be opsonized by binding of immunoglobuliln and complement factors to their surfaces; opsonized zymosan or latex will stimulate increased oxidant production by white cells after they are activated by exposure to immunocomplexes.

"Responsiveness" is a measure of the patient's ability to respond to a maximum stimulatory dose of immunocomplex.

BACKGROUND OF THE INVENTION

Rapid quantitation of'specific analytes in an individual's blood is critically important for the diagnosis of disease and its severity, often under emergency conditions. in the monitoring of the progression of pathological conditions and following the recovery process brought about by surgical and drug therapies. It is often important to know not only whether a specific analyte is presents but as well its level, in order to determine the present stage of a particular condition or disease in order to prescribe the most effective remedy at that particular stage. In the treatment of many diseases, a particular therapy may be ineffective or toxic if given at the wrong stage of the condition. For example, the levels of specific markers of cardiac muscle damage and the relationship among them may indicate that a patient has had or may be having a heart attack. The level of a therapeutic drug in the circulation may indicate whether the patient is being dosed optimally, and whether presumptive side effects are possibly due to excess levels of the drug. In infection and sepsis, the circulating levels of infectious microorganism-derived toxins and inflammatory mediators produced by the patient's white blood cells in response to these toxins may indicate the severity and level or stage of sepsis and help identify the most efficacious course of therapy. Quantitation of analytes under emergency conditions and using the information to prescribe a particular therapy may mean the difference between saving a patient's life and contributing to the patient's death. For example, in the case of infection, hospital and particularly intensive care unit patients who have acquired nosocomial infections as a result of peri- or post-operative immunosuppression or infections secondary to other disease proccssces, such as pancreatitis, hypotensive or hypovolemic shock, physical trauma, burn injury, or organ transplantation, and subsequently develop septic shock syndrome, have a mortality which has been quoted to range from 30–70% dcpending upon other co-incident complications. Despite the development of increasingly potent antimicrobial agents, the incidence of nosocomial infections and, in particular, infections leading to sepsis or septicemia, is increasing. The difficulty with many ol the promising therapeutic agients is that their window of opportunity and indications for use have not been adequately delineated largely due to a lack ot appropriate rapid and quantitative diagnostic procedures and partly due to a lack ol complete understanding of the pathogenesis of the sepsis syndrome.

The presence of bacteria, viruses or fungi or their cell wall components including gram-positive peptidoolycans, lipoteichoic and teichoic acids, and gram-negative endotoxin (lipopolysaccharide, LPS) in blood is indicative of an infection. In addition, the immune system's reaction to the presence of these foreign antioens by the production of pro-inflammatory cytokine mediators such as interleukin-1 (IL-1), tumor necrosis factor (TNF) and interleukin-6 (IL-6), is also indicative ol an infection. The quantity of these analytes in circulation may be used to indicate the severity and level or stage of sepsis. For instance, at an early stage of Gram-negative sepsis, LPS may be present at a concentration as low as 50 pg/ml of whole blood. At the next stage, sepsis has progressed and a mediator of sepsis, TNF, can be detected and measured using antibody against TNF. At stage 3. TNF may be present in smaller amounts since it is transitory and another transitory mediator, IL-1, may appear. As sepsis progresses further, LPS levels may decrease and TNF be absent, but IL-1 may increase and interleukin-6 (IL-6) may appear. Finally, in a more prolonged case of sepsis, LPS may be present and IL-1 may be at low levels but IL-6 may be at very high levels. Tlhus, diagnosis of sepsis and identifying its stage in the course the disease are critical for the successful treatment of this serious and potentially lethal consequence of infection. Quantitation of the levels of the sepsis-associated analytes provide information necessary to determine the best course of therapy to treat the acute disease.

Currently, one of the major problems with many of the therapeutic protocols being tested by the pharmaceutical companies conducting clinical trials in sepsis intervention is their inability to rapidly detect early and evolving sepsis. The results of blood cultures may arrive too late. Otlher septicaemia tests are also time consuming and may not be sensitive enough for early detection. Centocor Inc.'s immunometric assay for tumor necrosis factor-alpha (TNF-α). as described in WO 90/06314. uses two antibodies, one of which is labeled. The National Aeronautics and Space Administration detects P,seu(titmonloas bacteria by extraction of Azurin and detection using Azurin-specific antibody (U.S. Pat. No. 7,501,908). The endotoxin assay kit from Bio Whittaker (Walkerville, Md., U.S.A.) or Seikagaku Kogyo Ltd. (Tokyo Japan) is a Limulus Amebocyte Lysate (LAL) Assay technique which may be used as a comparison for the present invention.

Many investigators versed in the complexities of the septic response believe that treatment is ineffectual for patients who already manifest the classical clinical symptoms of sepsis (i.e., hyperdynamic circulation hypotension, decreased systemic vascular resistance, pyrexia and increased oxygen dependency). Thee course of the inflammatory process has progressed too far for many of the interventions to benefit the patient since the multiple interacting inflammatory cascades with which the body attempts to eliminate the infectious challenge are in many instances at their nadir and difficult to control pharmacologically. Thus, a major clinical and diagnostic challenge is to identify and stage patients, ideally early in the progression of the septic response, or to identity those patients at high risk of developing fulminant sepsis syndrome. The same therapeutic agents given at the one stage in the septic process may have more significant beneficial effects than when given at another, since it is clear that an optimal window period may exist for the efficacy of any particular therapeutic agent. For example, giving a patient antibodies or receptors directed against gram-negative endotoxins when the patient has no detectable levels of these agents present in the circulation and already has a maximally activated cytokine cascade is a waste of resources and of no benefit to the therapy of the patient. The potential market for these anti-sepsis strategies remains large (about 250,000 cases per year in the USA) and has been limited by the inability to identify and stage patients who could benefit from the appropriate pharmacologic interventions.

It is toward the development of improved methods for the rapid quantitation of analytes, particularly infection- and sepsis-related analytes, in a whole blood sample, that the present application is directed.

SUMMARY OF THE INVENTION

In its broadest aspect the present invention is directed to a method for measuring the amount of a preselected analyte in a sample of a bodily fluid comprising the steps of (a). forming an immunocomplex between the analyte and an antibody thereto; (b) reacting the immunocomplex with an oxidant-producing phagocytic cell in the presence of an activator; and (c) measLiring the amount of oxidant pr oduced as compared with that produced by a maximal amount of immunocomplexes between the analyte and the antibody, in the presence of the activator, as an indicator of the amount of the analyte in the sample. For example the bodily fluid may be whole blood. The oxidant-producing phagocytic cells are neutrophils, lymphocytes monocytes, or combinations. When the bodily fluid sample is whole blood, oxidant-producing phagocytic cells are present in the sample.

The activator may be. by way of non-limiting example, zymosan, latex particles, opsonized zymosan, opsonized latex particles. phorbol esters, N-formyl-met-leu-phe, or combinations. Thie amount of oxidant produced by the oxidant producing cells is achieved using a chemiluminescent compound which reacts with the oxidants to generate light. Non-limiting examples include luminol, lucigenin and pholasin. The antibody is monoclonal antibody of class IgM or IgG.

The analyte is any substance or component present in a bodily fluid sample which may participate in the formation of an antigenic-antibody complex (immunocomplex) with added, exogenous antibody. For example, analytes may include gram-positive bacteria, (gram-negative bacteria. fungi, viruses, gram-positive cell wall constituents, lipoteichoic acid, peptidoglycan, teichoic acid, gram-negative endotoxin, lipid A, hepatitis A, inflammatory mediators, drugs of abuse. therapeutic drugs, or cardiac markers, such as myoglobin, creatine kinase MB, troponin I or troponin T. Inflammatory mediators include but are not limited to tumor necrosis factor. Interleukin-1, interleukin-6, interleukin-8, interferon, and transforming growth factor β. The analyte may be one indicative of infection or indicative of sepsis.

In a preferred embodiment, the analyte is lipopolysaccharide, the antibody is anti-lipopolysaccharide antibody, the sample is a whole blood sample, and the activator is zymosan.

In a further aspect, the present invention is directed to a method for measuring the level of a preselected analyte present in a sample of a bodily fluid comprising the following steps i) providing three aliquots of the sample, designated aliquots A, B, and C;

ii) providing a source of oxidant-producing phagocytic cells and a source of complement proteins;

iii) providing aliquot B with an amount of anti-analyte antibody sufficient to form an immunocomplex with the analyte in the sample, to provide reaction aliquot B;

iv) providing aliquot A as a control to reaction aliquot B without added anti-analyte antibody, to provide reaction aliquot A;

v) providing aliquot C with a equivalent amount of the anti-analyte antibody as in reaction aliquot B, and in addition containing a maximal stimulatory amount of analyte, to provide reaction aliquot C;

vi) incubating reaction aliquots A, B, and C with oxidant-producing phagocytic cells and a source of complement proteins under suitable conditions and for a time sufficient for any immunocomplexes formed in the reaction aliquots to react with oxidant-producing phagocytic cells and complement proteins to produce oxidants;

vii) contacting a chemiluminescent compound which reacts with the oxidants to generate light with reaction aliquots A, B, and C, prior to or after step vi);

viii) measuring light emission from reaction aliquots A, B, and C over a predetermined time period under suitable conditions; and ix) correlating differences in light emission among reaction aliquots A, B3, and C as an indicator of the amount of analyte in the sample.

The aforementioned steps may be carried out following manual, semi-automated, or automated procedures. The test may provide results in a short period of time, such that the measurement of the analyte can be performed to aid in the rapid diagnosis of a patient's condition. Instrumentation may be provided that can be performed in the emergency room, at the bedside, or for home use. Depending on the assay format, a test may be performed in around 20 minutes or less.

By way of non-limiting examples, the bodily fluid in the aforementioned method may be whole blood, in which oxidant-producing phagocytic cells are present. Alternatively, a source of oxidant-producing phagocytic cells may be added, such as white blood cell fractions containing neutrophils. lymphocytes, monocytes, or combinations. An agent capable of increasing oxidant production by white blood cells on exposure to immunocomplexes may be included in reaction aliquots A, B, and C; this agent may be by way of non-limiting example, zymosan, latex particles, phorbol ester, N-formyl-met-leu-phe, opsonized zymosan, opsonized latex particles, or combinations thereof The chemiluminescent compound may be, for example, luminol, lucigenin or pholasin. The anti-analyte antibody may be a monoclonal antibody of class IgM or IgG.

The analyte is any substance or component present in a bodily fluid sample which may participate in the formation of an antigen-antibody complex (immunocomplex) with added, exogenous antibody. For example. analytes may include gram-positive bacteria, gram-negative bacteria, fungi, viruses, oiram-positive cell wall constituents, lipoteichoic acid, peptidoglycan, teichoic acid, gram-negative endotoxin lipid A, hepatitis A, inflammatory mediators, drugs of abuse. Therapeutic drugs, and cardiac markers, as described above. Inflammatory mediators include but are not limited to tumor necrosis factor, interleukin-1, interleukin-6, interleukin-8, interferon, and transforming growth factor β. The analyte may be one indicative of infection or indicative of sepsis.

In a preferred embodiment, the analyte is lipopolysaccharide, the antibody is anti-lipopolysaccharide antibody, the sample is a whole blood sample, and the activator is zymosan.

In a further aspect of the present invention. a diagnostic kit for measuring the level of a preselected analyte present within a sample of a bodily fluid is provided, comprising: a first container of IgM or IgG antibody specific to the preselected analyte; a second container of chemiluminescent compound; and a third container of analyte. A source of oxidant-producing phagocytic cells may be included in the kit for samples which do not contain them; the cells may be neutrophils, lymphocytes, monocytes, or combinations thereof. The diagnostic kit may also include additional container containing an agent capable of increasing, oxidant production by white blood cells on exposure to immunocomplexes, for example, zymosan, latex particles, phorbol ester, N-formyl-met-leu-phe, opsonized zymosan, opsonized latex particles, or combinations. The chemiluminescent compound may be luminol, lucigenin or pholasin.

In another aspect, the invention is directed to a method for determining the stage of sepsis of a patient from a sample of whole blood comprising the concurrent measurement of:
(a) the level of microbial products or inflammatory mediators; (b) the maximum oxidant production by the patient's neutrophils; and (c) the level of responsiveness of the patient's neutrophils to a maximum stimulatory level of immunocomplexes. These parameters are measured by the steps of i) providing three aliquots of said sample, designated aliquots A, B, and C;
ii) providing aliquot B with an amount of anti-analyte antibody sufficient to form an immunocomplex with the analyte in the sample, to provide reaction aliquot B;
iii) providing aliquot A as a control to reaction aliquot B without any added anti-analyte antibody, to provide reaction aliquot A;
iv) providing aliquot C with a equivalent amount of anti-analyte antibody as in reaction aliquot B. and in addition containing a maximal stimulatory amount of analyte, to provide reaction aliquot C;
v) incubating reaction aliquots A, B, and C with said oxidant-producing phagocytic cells and said source of complement proteins under suitable conditions and for a time sufficient for any immunocomplexes formed in the reaction aliquots to react with oxidant-producing phagocytic cells and complement proteins to produce oxidants;
vi) contacting a chemiluminescent compound which reacts with oxidants to generate light with reaction aliquots A, B, and C, prior to or after step vi);
vii) measuring light emission from reaction aliquots A, B, and C over a predetermined time period under suitable conditions; and
viii) correlating differences in light emission among reaction aliquots A, B, and C as an indicator of the level of microbial products or inflammatory mediators; the maximum oxidant production by the patient's neutrophils; and the level of responsiveness of the patient's neutrophils to a maximum stimulatory level of immunocomplexes; and
ix) determining the patient's stage of sepsis from the aforementioned levels.

The non-limiting selections of components for the steps listed above are those described hereinabove.

DETAILED DESCRIPTION OF THE INVENTION

Figure 1:
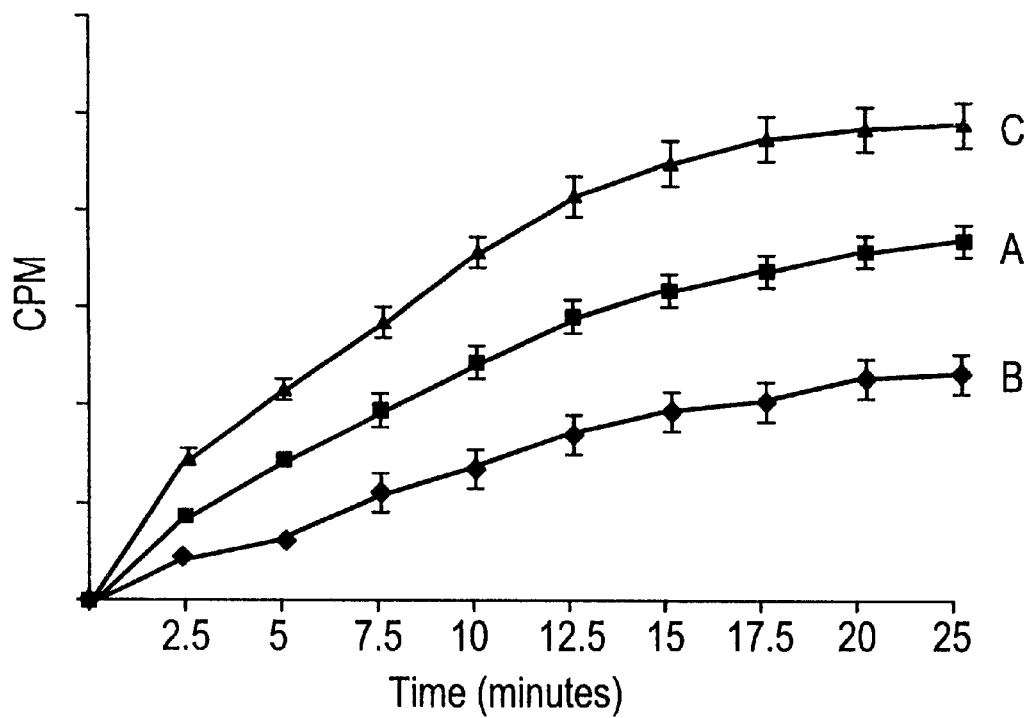
FIG. 1 depicts a typical, whole-blood chemiluimiinescenice profile of a sample from a patient with endotoxcemiia. Curve A represents whole blood plus zymosan; B, whole blood plus zymosan plus anti-endotoxin antibody; and C, whole blood plus zymosan plus anti-endotoxin antibody plus cxogcnous endotoxin (800 pg/ml).

The present invention relates to a method for measuring the level of a preselected analyte in a sample of a bodily fluid, such as whole blood of a mammal, including humans, by incubating the test sample with an antibody specific to the analyte to form an immunocomplex, which then interacts with phagocytic cells present in or added to the sample and result in the production of oxidants. Oxidants may be detected using chemiluminescent reagents added to the sample. The phagocytic cell oxidant response may be optionally enhanced by the inclusion of selected activator agents such as zymosan. Thee level of chemiluminescence elicited from oxidant-producing phagocytic cells by a particular level of immunocomplexes is related to the maximal chemiluminescent elicited from phagocytic cells by a maximal amount of immunocomplexes. In order for the assay to provide a readout of the amount of analyte in the sample, the present invention utilizes a separate measure of the maximal responsiveness of the phagocytic cells in the sample to immunocomplexes, and the ratio of oxidant production by immunocomplexes formed from the analyte to oxidant production by a maximal amount of analyte-antibody immunocomplexes provides a relative measure of the amount of analyte in the sample. This method may be used to determine levels of an analyte in a blood sample, such as endotoxin and other analytes related to sepsis, in order to assess severity and level or, in combination with other parameters derivable from the assay herein, the stage of sepsis of the patient, and to direct and monitor the proper therapeutic course. The assay may also be used to measure the level of other preselected analytes present in a blood sample, such as hormones, acute phase proteins, toxins. drugs of abuse, markers of cardiac muscle damage, therapeutic drugs, cytokines, cheemokines, etc. Any analyte in the sample for which an antibody can be added that forms an immunocomplex capable of stimulating oxidant production by phagocytic cells can be measured in the assay of the present invention.

The present invention utilizes a three-aliquot assay lormat for the measurement of the preselected analyte. All three aliquots include an optional activator or enhancer of oxidant production, Such as zymosan. Two aliquots include antibodies to the analyte, of which one also contains added analyte to provide the maximal amount of immunocomplexes. Sample is added to all three tubes. Non-limiting examples of details as to preincubation and equilibration times, incubation times with the various components of the assays, preincubations and reaction times are provided below, and, with the benefit of this disclosure., can be readily determined by the skilled artisan to maximize the sensitivity and rapidity of the assay. Details as to the order in which the aliquots are prepared, samples are incubated and subdivided, are provided for illustration purposes only and can be modified.

The aforementioned assay may be canried out following manual, semi-automated, or automated procedures. The test may provide results in a short period of time, such that the measurement of the analyte can be performed to aid in the rapid diagnosis of a patient's condition. Instrumentation may be provided that can be performed in the emergency room, at the bedside, or for home use, among others. Depending on the assay format, a test may be performed in around 20 minutes or less.

In gencral, the assay is carried out as follows. The assay readout for a particular analyte is provided in units of activity. In the example of endotoxin as the analyte of interest, the assay readout is endotoxin activity, or EA. The assay may be modified for automation, or semi-automation, and performed in any order or sequence which provides equivalent data. For example. two aliquots of whole blood are dispensed into suitable tubes that are free of any contaminants or other materials that may adversely influence the outcome of the test. The tubes are placed in a incubator or other equivalent device in which the temperature of all three tubes may be maintained similarly, to keep the conditions the same among the tubes. For example, a thermostatted aluminum block pre-heated to about 37° C. may be used. One tube contains an amount olthe analyte to maximally stimulate oxidant production when combined, in a subsequent step, with antibody to the analyte. The other tube contains no additives. These tubes are incubated for about 10 min. at 37° C. During the last 5 minutes of this incubation assay three tubes per assay tubes are loaded into the heating block. One tube, herein referred to as Tube A, contains a control reagent used for antibody stabilization or no reagent at all, Tubes B and C contain the same amount of antibody to the analyte. To each tube a mixture of buffer containing the chemiluminescent compound, optionally with the stimulant, such as non-opsonized zymosan, is added. Theis mixture is temperature equilibrated for at least about 5 min. After the blood has incubated for a total of about 10 min. at about 37° C., an equal volume, for example 20 µl, is transferred into assay tubes A and B from the blood tube with no LPS and the same volume, in this example, 20 µl, is transferred from the blood tube containing LPS into assay tube C. All tubes are mixed well and placed in the chemiluminometer for reading. The luminometer is thermostatted at about 37° C. and the assay is read for a total of about 20 min. Individual tube light integrals are calculated and the analyte activity, for example, EA is determined by the calculation:

$$\text{Activity} = 100 \times \frac{\text{Light Integral Tube } B - \text{Light Intergral Tube } A}{\text{Light Integral Tube } C - \text{Light Intergral Tube } A}.$$

Thee various components and conditions described above may be tailored to the specific analyte being measured. The amount of components, the lengths of preincubation and incubation, the period of time over which the luminescence is read, the temperatures and other parameters of the assay may be adjusted by the skilled artisan within the range of operability of the particular assay. Numerous variations in the examples provided are embraced herein.

Thie various components of the assay are as follows.

Preselected analyte. The analyte is any substance or component present in a bodily fluid sample which may participate in the formation of an antigen-antibody complex (immunocomplex) with added, exogenous antibody. For example, analytes may include gram-positive bacteria. gram-negative bacteria, fungi, viruses, gram-positive cell wall constituents, lipoteichoic acid, peptidoglycan, teichoic acid, gram-negative endotoxin, lipid A, hepatitis A, inflammatory mediators, drugs of abuse, therapeutic drugs, or cardiac markers, such as myoglobin, creatine kinase MB, troponin I or troponin T. Inflammatory mediators include but are not limited to tumor necrosis factor. Interleukin-1, interleukin-6. Interleukin-8, interferon, and transforming growth factor β. The analyte may be one indicative of infection or indicative of sepsis.

In a preferred embodiment, the analyte is lipopolysaccharide, the antibody is anti-lipopolysaccharide antibody, the sample is a whole blood sample, and the activator is zymosan.

Anti-analyte antibody. The antibody against the preselected analyte of the present method is preferably of the IgM class. IgM-analyte immunocomplexes trigger a reaction sequence which results in the stimulation of white blood cell oxidant production via complement pathway activation. The antibody against the analyte can also be of the IgG class.

For the detection of LPS (endotoxin), Xomen-F5, a commercially-available murine monoclonal IgM pentamer directed against a lipid A component of gram-negative endotoxin, produced by Xoma, Palo Alto, Calif., is suitable.

The antibody may be provided in a stabilized liquid or solid form, for example, lyophilized in bead form with the stabilizing agent trehalose. A non-limitinig example of such a bead form is described in copending application Serial No. (Attorney's Docket Number 1112-1-999), incorporated herein by reference.

Optional white cell stimulant. Although stimulants such as zymosan or latex beads are not required additions to the test procedure, the chemiluminescence produced by immunocomplexes in the test sample is enhanced by such inclusion. Zymosan and latex beads enhance the chemiluminescent response by stimulating concerted white cell oxidant production and phagocytosis. This stimulation may be further enhanced if the zymosan or latex beads are opsonized, through the binding of immunoglobulin G and complement factors (iC3b and C3b). Thee addition of zymosan or latex acts as an amplification process to increase oxidant production and is preferred in the practice of the present invention, but is not obligatory for the recognition of immunocomplexes by white blood cells. Theere are many kinds of latex beads depending upon the polymner from which they are prepared which can be utilized in the practice of this invention. These include, for example, polystyrene, styrene divinylbenzene, and acrylic acid polymers; polystyrene is preferred.

Further examples of suitable stimulants include phorbol esters, such as phorbol 12-myristate 13-acetate, and peptides such as N-formyl-methionine-leucine-phenylalanine, abbreviated fMLP or N-formyl-met-leu-phe.

Chemiluminescent indicator. The phenomenon of chemiluminescent resulting from the production of neutrophil oxidants is described by Allen, R. C. *Methods in Enzymology* 133:449 (1986) using the acyl azide dye luminol as a light emitting agent. This technique permits the sensitive measurement of neutroplil respiratory burst activation using) small numbers of polymorphonuclear leukocytes or later even white cells in whole blood. Other chemiluminescentt dyes which produce light as a result of neutrophil oxidant production have also been identified including lucigenin and pholasin; others will be known by the skilled artisan.

Oxidant-producin phagocytic cells. If whole blood samples are used, or other bodily fluid samples containing white blood cells, oxidant-producing phagocytic cells are already present in the sample. Whole blood is the preferred bodily fluid. For samples without such cells or too little to provide a means for producing oxidants proportional to the amount of immunocomplexes, phagocytic cells can be added to the sample.

Appropriate cells include but are not limited to neutrophils, lymphocytes, and monocytes. These cells may be derived from another sample, cell culture, artificially prepared cells, and other source.

Immunocomplexes to maximally stimulate white blood cells. Inclusion in the assay described herein of a measure of the maximal response to a maximal stimulatory level of immunocomplexes, by the white blood cells present in or added to the sample, enables the present invention to provide a measure of the amount of analyte in the sample. This measure may be achieved with any antigen and corresponding anti-antigen antibody that achieves the desired stimulation, such as endotoxin and anti-elndotoxin antibody. Antibodies of the IgM class are preferred. For simplification of the assay, the same analyte as the preselected analyte is preferably used. For example, for a LPS assay, all three tubes contain zymosan; two tubes contain the same amount of anti-LPS antibodies, of which one tube also contains an amount of LPS which forms a maximal amount of immunocomplexes with the anti-LPS. The sample, whole blood containing an unknown amount of LPS, is added in equal amounts to all three tubes. All tubes contain a reagent which produces light in response to oxidants. White blood cells in the sample provide the oxidants in response to immunocomplexes. The first tube, containing sample and zymosan only, produces a background level of chemiluminescent. The second tube, containing zymosan. sample LPS, and anti-LPS antibodies, produces a level of chemiluminescence proportional to the amount of analyte, LPS, in the sample. The third tube, containing zymosan, sample LPS, added maximal LPS, and anti-PS antibodies, produces a maximal amount of chemiluminescence. As will be seen below, the ratio of the integrated chemiluminescent of the second tube, minus that of the control tube, to the integrated chemiluminescent of the third tube. minus that of the same control, provides the readout of the relative amount of LPS in the sample.

For samples that do not contain white blood cells capable of producing oxidants in response to immunocomplexes, suitable white blood cells or equivalent cells from another source, such as a whole blood sample, cultured white blood cells, or other white cells, artificially prepared cells, and other source.

Assay procedure. The following procedure is a non-limiting example of a protocol that may be followed to provide a rapid and sensitive assay for endotoxin (LPS). The assay readout is endotoxin activity, or EA. Thee assay may be modified for automation, or semi-automation, and performed in any order or sequence which provides equivalent data. In the following example, two aliquots of blood (500 $\mu$l) are dispensed into depyrogenated glass tubes into a thermostatted aluminum block pre-heated to 37° C. One tube contains LPS as a maximum calibrator the other tube contains no additives. Theese tubes are incubated for 10 min. at 37° C. During the last 5 minutes of this incubation glass or polystyrene assay tubes are loaded into the heating block. Three tubes are used per assay. Tube A contains a control reagent used for antibody stabilization or no reagent at all, Tubes B and C contain antibody. To each tube a mixture of Luminol Buffer with unopsonized zymosan is added (500 $\mu$l per tube). This mixture is temperature equilibrated for at least 5 min. After the blood has incubated for a total of 1 0 min. at 37° C., 20 $\mu$l is transferred into assay tubes A and B from the blood tube with no LPS and 20 $\mu$l is transferred from the blood tube containing LPS into assay tube C. All tubes are vortexed and placed in the chemiluminomcter for reading. The luminometer is thermostatted at 37° C. and the assay is read for a total of 20 min. The luminometer cumulates the light output of each tube over time and provides an integral of the light output. From the Individual tube light integrals, the endotoxin activity, EA, is calculated using the formula:

$$EA = \frac{\text{Light Integral Tube } B - \text{Light Integral Tube } A}{\text{Light Integral Tube } C - \text{Light Integral Tube } A}.$$

In this manner the EA is calculated and the decision of whether a patient is endotoxernic or not is based on a cutoff value of range. The clinical cutoff value may be chosen on the basis of epidemiological studies on the particular analyte of interest, and the sensitivity and specificity of the particular assay components, to provide normal and abnormal ranges, cutoff values, as well as the positive and negative predictive values of the assay. Under a particular set of operating conditions provdled herein by way of non-limitillg example, a value of >35 EA, would indicate clinically significant endotoxemia.

As noted above, other analytes may be determined utilizing the methods of the present invention. The levels of such other analytes may also be expressed in relative units, expressed as a ratio to maximal chemiluminescence. as corrected by background. For example, cardiac markers to identify the cause of chest pain and distinguish unstable ang,ina from a heart attack, using combinations of markers including myoglobin, creatine kinase MB, troponin I or troponin T. and other cardiac specific and skeletal muscle specific markers for ruling in or ruling out heart attack, are embraced within the present invention.

As mentioned above, various automated and semiautomated methods may be used with adaptations of the present invention. For example, chemiluminescent of the three tubes may be determined serially, in an instrument that reads a single channel, by the appropriate timing and addition of reagents to the appropriate tubes, with the appropriate pre-incubation times. A single whole blood sample may be used successively for determining the background chemiluminescenice, that of the sample analyte, and lastly, the maximal stimulatory dose. A multichannel luminometer may subtract the background values during measurement. Thie assays also may be adapted to a thin film format, rather than liquid in tubes, to facilitate the automation and simplification of assay. For example, a test strip-like device may be prepared with three separate fluid paths, to conduct a whole blood sample, such as that obtained by finger prick, to three separate regions, each of which has the appropriate reagents corresponding to tubes A, B, and C as described above. The strip may be inserted into a luminometer device. such as a handheld device. In another embodiment, the reagents used to detect the level of the phagocyte oxidant burst yields a chromogen, visible or fluorescent, the density of which is proportional to the oxidant level and. proportionately the immunocomplex level. Reflectometry may be used to quantitate the color and calculate the analyte level. These and other variations on the invention are embraced herein.

As mentioned above. the quantity of infection or sepsis related analytes in circulation may be used to indicate the severity and level or stage of sepsis. In addition, the present assay may be used to add additional parameters to the diagnosis of stage of sepsis. The maximum oxidant production of neutrophils, as measured by CLmax, is a measure of t he ability of the white blood cell to respond to programmed opsonic challenage. The responsiveness of the patient's neutrophils to immlubocomplexes, termed responsiveness, is a measure of the maximal abilitv of the white blood cell to bind and respond to opsonized immunocomplexes. A large responsiveness is indicative of a large response reserve for processing opsonied immunocomplexes and is viewed as the normal healthy state. A small responsiveness represents a diminished reserve for processing opsonized immunocomplexes and is indicative of an immunocompromised or diseased state. Lack of a robust response in an indication of anergy, the inability of the immune system to mount an effective immune response. In the final stage of anergy in sepsis, during the terminal stage of the condition, the patient's immune system is progressively weakening in its ability to combat microbial infection. Patients progressing to this latter stage suffer a very poor prognosis.

The examples below describe several methods of practicing the invention, such as varying the order in which to add the reagents, varying blood dilutions, and omitting zymosan. Modifications of these protocols while within the scope of the invention, may be conceived by the skilled artisan. In place of a whole blood sample, a subfraction of white blood cells, such as neuitrophils or lymphocytes or mollocytes, may be used as a substrate. A chemiluminescent compound other than luminol may be used, such as, lucigenin or pholasin.

EXAMPLE I

Measurement of LPS

To measure the amount of endotoxin in a sample of whole blood. the following reaction aliquots were prepared:

A=Whole blood+zymosan
B=Whole blood+zymosan+anti-LPS antibody
C=Whole blood+zymosan+anti-LPS antibody+ exogenous LPS (800 pg/ml)

All reaction aliquots contained zymosan in order to optimize oxidant production of the patient's white blood cells in response to immunocomnplexes. In addition to the patient's blood sample and zymosan, tube B contained antibody against the analyte to be measured, in this case endotoxin. Tube A served as a control to tube B. In order to determine the maximal response of the patient's white blood cells to immunocomplexes, tube C contained a maximal stimulatory amount of immunocomplexes, derived from the same amount of anti-endotoxin antibody as in tube B, with the addition of LPS from $E.\ coli$ 055:B5 (determined to be 800 pg/ml or 0.67 EU/ml at an antibody concentration of 0.4 $\mu$g/assay). While in this example the antigen used to form immunocomplexes to determine maximal response (endotoxin-anti-endotoxin) was identical to the analyte, this does not need to be the true for all analytes, although it is most convenient to do so.

The following materials were used and methods followed in carrying out the assay. Variations in the components described here as well as the procedures may be modified by standard procedures without deviating from the invention.

All glass surfaces used for endotoxin assay or storage of reagents for endotoxin assay including assay tubes were depyrogenated by heating to 300° C. for at least 6 hours. All polystyrene and polyethylene surfaces used for storage of antibodies, HBSS-luminol or blood products were sterile and essentially endotoxin free as determined by chromogenic LAL assay of pyrogen free water left in contact with the surface of interest. All pipette tips used for fluid transfer were sterile and pyrogen free (Diamed, Mississauga, Ontario, Canada). Blood samples used for the assay were drawn by venipuncture or through indwelling arterial lines into sterile 3 ml EDTA anti-coagulated Vacutainer tubes (Becton Dickenson, Franklin Lakes, N.J.) which were pretested for LPS content (less than 0.005 EU/ml).

Luminol (5-amino-2,3-dihydro-1,4-phthalazinedione, free acid), zymosan A ($Saccharomyces\ cerevisiae$), lipopolysaccharides from $Escherichia\ coli$ ($E.\ coli$) serotypes (026:B6. 055:B5, 0111:B4) (gram-negative endotoxin), and lipoteichoic acids from Streptococcus spp. (Gram-positive cell wall constituent) were purchased from Sigma (Sigma Chemical Co., St. Louis, Mo.).

Buffer for measurement of whole blood or white cell chemiluminescent studies was HBSS (pyrogen free, endotoxin less than 0.005 EU/ml) containing 1.5 mM calcium salt and 0.9 mM magnesium salt (Gibco BRL, Grand Island, N.Y.). This buffer (500 ml) was vigorously mixed overnight at 25° C. with luminol to yield a saturated solution (150 $\mu$M, HBSS-luniinol) and then supplemented with 4 U/ml of lithium heparin.

All chemiluimiinescenice experiments were assayed in triplicate and the results expressed as the mean luminometer counts per minute ±1 SD. Assays may also be prepared using duplicate or single tubes for reaction tubes A, B and C.

The following assay protocol was followed. Two aliquots of blood (500 $\mu$l) are dispensed into depyrogenated glass tubes into a thermostatted aluminum block pre-heated to 37° C. One tube contained a maximal dose of LPS; the other tube is empty. These tubes are incubated for 10 min. at 37° C. During the last 5 minutes of this incubation glass or polystyrene assay tubes are loaded into the heating block. Three tubes are used per assay. Tube A contains control reagent used for antibody stabilization or no reagent at all, Tubes B and C contain antibody. To each tube a mixture of Luminol Buffer with unopsonized zymosan is added (500 $\mu$l per tube). This mixture is temperature equilibrated for at least 5 min. After the blood has incubated for a total of 10 min. at 37° C., 20 $\mu$l is transferred into assay tubes A and B from the blood tube with no LPS and 20 $\mu$l is transferred from the blood tube containing LPS into assay tube C. All tubes are vortexed and placed in the chemiluminometer for reading. The luminometer is thermostatted at 37° C. and the assay is read for a total of 20 min.

A typical whole blood chemiluminescent profile of a patient with enidotoxemia is shown in FIG. 1. The 20-miinute light integrals of tubes A, B and C are used to calculate the amount of LPS in the sample as follows. The amount of LPS present in the sample is referred to as "eidotoxin Activity" (EA) and calculate from the light integrals as follows:

$$EA = 100 \times \frac{\text{Light Integral Tube } B - \text{Light Integral Tube } A}{\text{Light Integral Tube } C - \text{Light Integral Tube } A}.$$

In this manner the EA is calculated and the decision of whether a patient is endotoxemic or not may be based on a cutoff value of range, i.e. >35 EA. an indicator of of clinically significant endotoxemia.

Further parameters are available from the three-tube assay results as pertains to the stage of sepsis. Responsiveness (R) of the patients white blood cells, a measure of the maximal ability of the white blood cell to bind and respond to opsonized immunocomplexes as defined above, is calculated as follows:

$$R = 1 - \left[\frac{\text{Light Integral Tube } A}{\text{Light Integral Tube } C}\right].$$

Furthermore, a measure of the level of white blood cell activation and cell number ($CL_{max}$) may be measured as the peak luminiometer count rate of tube A during the course of the assay. The maximum oxidant production of neutroplhils, as measured by CLmax, is a measure of the ability of the white blood cell to respond to programmed opsonic challenge.

The followingi data in Table 1 is (renerated froim the experimente Explanations for the calculations of B-A, C-A, EA, and Responsiveness are provided above.

TABLE 1

| Sample | Light Integral | | | B-A | C-A | EA | Responsiveness |
| --- | --- | --- | --- | --- | --- | --- | --- |
| | Tube A | Tube B | Tube C | | | | |
| 1 | 0.054 | 0.122 | 0.154 | 0.068 | 0.099 | 68 | 65 |
| 2 | 0.045 | 0.067 | 0.119 | 0.022 | 0.074 | 30 | 62 |
| 3 | 0.047 | 0.077 | 0.096 | 0.030 | 0.049 | 62 | 51 |
| 4 | 0.095 | 0.186 | 0.180 | 0.092 | 0.085 | 107 | 47 |
| 5 | 0.096 | 0.202 | 0.269 | 0.106 | 0.173 | 61 | 64 |
| 6 | 0.068 | 0.124 | 0.128 | 0.056 | 0.060 | 93 | 47 |
| 7 | 0.054 | 0.122 | 0.154 | 0.068 | 0.099 | 68 | 65 |
| 8 | 0.031 | 0.040 | 0.137 | 0.009 | 0.105 | 8 | 77 |
| 9 | 0.033 | 0.083 | 0.141 | 0.050 | 0.107 | 46 | 76 |
| 10 | 0.292 | 0.711 | 1.112 | 0.419 | 0.820 | 51 | 74 |
| 11 | 0.074 | 0.126 | 0.251 | 0.053 | 0.177 | 29 | 71 |
| 12 | 0.038 | 0.105 | 0.174 | 0.067 | 0.136 | 49 | 78 |
| 13 | 0.266 | 0.828 | 1.882 | 0.562 | 1.616 | 34 | 86 |
| 14 | 0.612 | 1.552 | 1.442 | 0.940 | 0.830 | 113 | 58 |
| 15 | 0.290 | 0.412 | 0.692 | 0.122 | 0.401 | 30 | 58 |
| 16 | 0.042 | 0.073 | 0.235 | 0.031 | 0.193 | 16 | 82 |
| 17 | 0.231 | 0.395 | 0.589 | 0.164 | 0.358 | 46 | 61 |
| 18 | 0.047 | 0.285 | 0.965 | 0.238 | 0.918 | 26 | 95 |

While the invention has been described and illustrated herein by references to various specific material, procedures and examples, it is understood that the invention is not restricted to the particular material combinations of material, and procedures selected for that purpose. Numerous variations of such details can be implied as will be appreciated by those skilled in the art.

What is claimed is:

1. A method for measuring a level of a preselected analyte present in a sample of a bodily fluid comprising:
   i) providing three aliquots of said sample, designated aliquots A, B, and C;
   ii) providing a source of white blood cells and a source of complement proteins;
   iii) providing aliquot B with an amount of anti-analyte antibody sufficient to form a detectable immunocomplex with said analyte in the sample, to provide reaction aliquot B;
   iv) providing aliquot A as a control to reaction aliquot B without said anti-analyte antibody, to provide reaction aliquot A;
   v) providing aliquot C with a equivalent amount of anti-analyte antibody as in reaction aliquot B, and in addition containing a maximal stimulatory amount of analyte, to provide reaction aliquot C;
   vi) incubating reaction aliquots A, B, and C with said white blood cells and said source of complement proteins under suitable conditions and for a time sufficient for any immunocomplexes formed in the reaction aliquots to react with white blood cells and complement proteins to produce oxidants;
   vii) contacting a chemiluminescent compound which reacts with said oxidants to generate light with reaction aliquots A, B, and C, prior to or after step vi);
   viii) measuring light emission from reaction aliquots A, B, and C over a predetermined time period under suitable conditions; and
   ix) correlating differences in light emission among reaction aliquots A, B, and C in accordance with the ratio $$100 \times \frac{(\text{light emission of aliquot } B) - (\text{light emission of aliquot } A)}{(\text{light emission of aliquot } C) - (\text{light emission of aliquot } A)}$$

as an indicator of the amount of said analyte in said sample.

2. The method of claim 1 wherein said sample is whole blood.

3. The method of claim 1 wherein said white blood cells comprise a white blood cell fraction derived from whole blood, said fraction selected from the group consisting of neutrophils, lymphocytes, monocytes, and combinations thereof.

4. The method of claim 1 wherein an agent capable of increasing oxidant production by white blood cells on exposure to immunocomplexes is included in reaction aliquots A, B, and C.

5. The method of claim 4 wherein said agent is selected from the group consisting of zymosan, latex particles, phorbol ester, N-formyl-met-leu-phe, opsonized zymosan, opsonized latex particles and combinations thereof.

6. The method of claim 1 wherein said chemiluminescent compound is selected from the group consisting of luminol, lucigenin and pholasin.

7. The method of claim 1 wherein said anti-analyte antibody is a monoclonal antibody of class IgM or IgG.

8. The method of claim 1 wherein said analyte is selected from the group consisting of gram-positive bacteria, gram-negative bacteria, fungi, viruses, gram-positive cell wall constituents, lipoteichoic acid, peptidoglycan, teichoic acid, gram-negative endotoxin, lipid A, hepatitis A, inflammatory mediators, drugs of abuse, therapeutic drugs, and cardiac markers.

9. The method of claim 8 wherein said inflammatory mediator is selected from the group consisting of tumor necrosis factor, interlcukin-1, Interleukin-6, Interleukin-8, interferon, and transforming growth factor β.

10. The method of claim 1 wherein said analyte is indicative of infection.

11. The method of claim 1 wherein said analyte is indicative of sepsis.

12. The method of claim 1 wherein said analyte is lipopolysaccharides, and said anti-analyte antibody is anti-lipopolysaccharides antibody.

13. The method of claim 12 wherein an agent capable of increasing oxidant production by white blood cells on exposure to immunocomplexes is included in reaction aliquots A, B, and C.

14. The method of claim 13 wherein said agent is selected from the group consisting of zymosan, latex particles, opsonized zymosan, opsonized latex particles, and combinations thereof.

15. The method of claim 14 wherein said agent is zymosan.

* * * * *